United States Patent
McClintock

(10) Patent No.: US 10,869,693 B2
(45) Date of Patent: Dec. 22, 2020

(54) SPINAL CORRECTION SYSTEM AND METHOD OF USE THEREOF

(71) Applicant: K2M, Inc., Leesburg, VA (US)

(72) Inventor: Larry McClintock, Gore, VA (US)

(73) Assignee: K2M, Inc., Leesburg, VA (US)

( * ) Notice: Subject to any disclaimer, the term of this patent is extended or adjusted under 35 U.S.C. 154(b) by 158 days.

(21) Appl. No.: 16/071,212

(22) PCT Filed: Jan. 19, 2017

(86) PCT No.: PCT/US2017/014114
§ 371 (c)(1),
(2) Date: Jul. 19, 2018

(87) PCT Pub. No.: WO2017/127532
PCT Pub. Date: Jul. 27, 2017

(65) Prior Publication Data
US 2020/0085471 A1    Mar. 19, 2020

Related U.S. Application Data

(60) Provisional application No. 62/280,202, filed on Jan. 19, 2016.

(51) Int. Cl.
| | |
|---|---|
| *A61B 17/70* | (2006.01) |
| *A61B 17/88* | (2006.01) |
| *A61B 17/86* | (2006.01) |

(52) U.S. Cl.
CPC ...... *A61B 17/7022* (2013.01); *A61B 17/7031* (2013.01); *A61B 17/7032* (2013.01); *A61B 17/8625* (2013.01); *A61B 17/8869* (2013.01)

(58) Field of Classification Search
CPC ............ A61B 17/7022; A61B 17/7031; A61B 17/7032; A61B 17/8625; A61B 17/8869
USPC ................................................. 606/263, 279
See application file for complete search history.

(56) References Cited

U.S. PATENT DOCUMENTS

| | | | |
|---|---|---|---|
| 6,296,643 B1 | 10/2001 | Hopf et al. | |
| 7,942,910 B2 | 5/2011 | Doubler et al. | |
| 2003/0083657 A1* | 5/2003 | Drewry .............. | A61B 17/7031 606/254 |
| 2005/0143823 A1 | 6/2005 | Boyd et al. | |

(Continued)

OTHER PUBLICATIONS

International Search Report and Written Opinion issued in PCT/US2017/014114 dated Mar. 27, 2017.

*Primary Examiner* — Eduardo C Robert
*Assistant Examiner* — David C Comstock
(74) *Attorney, Agent, or Firm* — Lerner, David, Littenberg, Krumholz & Mentlik, LLP

(57) ABSTRACT

A spinal correction system includes a tensioning member and a fulcrum tensioner device including a housing defining a chamber having a biasing member therein and a camming pin operatively coupled with the biasing member. The tensioning member is configured to be received in the biasing member and looped around the camming pin, such that a first end of the tensioning member is oriented in a first direction and a second end of the tensioning member is oriented in a second direction. The camming pin is transitionable between an extended position in which the biasing member applies tension to the tensioning member and a retracted position in which the biasing member is compressed to inhibit application of tension to the tensioning member.

28 Claims, 16 Drawing Sheets

(56) References Cited

U.S. PATENT DOCUMENTS

| | | |
|---|---|---|
| 2006/0178693 A1 | 8/2006 | Hamada |
| 2008/0140202 A1 | 6/2008 | Allard et al. |
| 2010/0094358 A1 | 4/2010 | Moore et al. |
| 2013/0325065 A1* | 12/2013 | Malandain ......... A61B 17/7062 |
| | | 606/248 |
| 2014/0257397 A1 | 9/2014 | Akbarnia et al. |
| 2015/0201973 A1* | 7/2015 | Lindemann ........ A61B 17/7053 |
| | | 606/263 |
| 2015/0289906 A1* | 10/2015 | Murray .............. A61B 17/7028 |
| | | 606/263 |
| 2016/0262806 A1* | 9/2016 | Hsu .................... A61B 17/7076 |

* cited by examiner

SPINAL CORRECTION SYSTEM AND METHOD OF USE THEREOF

CROSS-REFERENCE TO RELATED APPLICATION

This application claims priority to, and the benefit of, U.S. Provisional Patent Application Ser. No. 62/280,202, filed on Jan. 19, 2016, the entire contents of which are incorporated by reference herein.

BACKGROUND

1. Technical Field

The present disclosure relates to a spinal deformity correction device and, more particularly, to a spinal correction system and methods for securing a spinal deformity correction device on a spine.

2. Discussion of Related Art

The spine is made up of a superposition of vertebrae that are normally aligned along a vertebral axis, extending from the lumbar vertebrae to the cervical vertebrae. There are many known spinal conditions, e.g., scoliosis, that require the imposition and/or maintenance of corrective forces on the spine in order to return the spine to its normal condition. When an individual's spine presents abnormal curvature, the vertebrae are inclined relative to one another and relative to said vertebral axis. The lateral edges of the vertebrae situated on one side are thus closer to one another and form a concave curve, while the lateral edges on the other side appear spaced apart from one another and form a convex curve. In order to straighten the spinal column, the lateral edges of the vertebrae on the concave side are spaced apart from one another and are taken relative to one another to a distance that is substantially equivalent to the distance between the lateral edges on the other side. Thereafter, in order to keep the vertebrae in that position relative to one another, known devices such as spinal rods, screws, and hooks are utilized.

Numerous alignment systems devices have been developed for use in spinal fixation. One type of spinal construct may include, for example, one or more spinal rods that can be placed parallel to the spine with fixation devices (such as hooks, screws, or plates) interconnected between the spinal rods at selected portions of the spine. The spinal rods can be connected to each other via cross-connecting members to provide a more rigid support and alignment system. Another such system may involve the use of springs that wrap around the outside of the vertebral bodies. Such springs may become entangled in the anatomy and become less effective as correcting the anatomy or may potentially break and become a projectile inside the anatomy causing further damage. While the aforementioned spinal fixation devices are suitable for some cases and typical rods and screws are able to correct some deformities, they are mainly effective at correcting deformities in the sagittal plane.

Therefore, a continuing need exists for a device or system that can safely and reliably correct deformities of vertebral rotation while restoring sagittal and coronal balance.

SUMMARY

The present disclosure is directed to a system for correcting abnormalities in spinal curvature without inducing a fusion of the vertebrae and without inhibiting the normal growth of the spine. A spinal correction system in accordance with an embodiment of the present disclosure includes a tensioning member and a fulcrum tensioner device. The fulcrum tensioner device includes a housing and a camming pin. In particular, the housing defines a chamber having a biasing member therein. The camming pin is operatively coupled with the biasing member. The tensioning member is configured to be received in the biasing member and looped around the camming pin such that a first end of the tensioning member is oriented in a first direction and a second end of the tensioning member is oriented in a second direction. The camming pin is transitionable between an extended position in which the biasing member applies tension to the tensioning member and a retracted position in which the biasing member is compressed to inhibit application of tension to the tensioning member.

In embodiments, the fulcrum tensioner device may include a securing portion defining a bore configured to receive a screw to secure the fulcrum tensioner device to a vertebral body.

In embodiments, the housing may define a longitudinal axis and a slot extending along the longitudinal axis. The slot may be configured to slidably receive the camming pin.

In embodiments, the fulcrum tensioner device may further include a cap defining a bore dimensioned to receive the camming pin. The cap may be configured to retain the biasing member within the chamber of the housing.

In embodiments, the camming pin may be biased towards the extended position.

In embodiments, the system may further include a fixation member including a cannulated screw defining a passage dimensioned to receive the tensioning member. The cannulated screw may include a housing and a shaft extending distally from the housing. The housing may include a recess dimensioned to receive the tensioning member. The fixation member may further include a set screw having a base portion and a threaded portion rotatably coupled with the base portion. The threaded portion may be configured to threadably engage an inner surface of the housing of the cannulated screw. The base portion may include a planar surface adapted to engage the tensioning member.

The base portion may have a non-circular cross-section to inhibit rotation of the base portion when disposed in the housing of the cannulated screw. The securing member may define a groove configured to guide the tensioning member. The fulcrum tensioner device may further include a release tab dimensioned to be received in the camming slot to maintain the camming pin in the retracted position.

In embodiments, the securing portion may include a screw configured to secure the fulcrum tensioner device to a vertebral body. The tensioning member may be formed of a flexible material.

In accordance with another embodiment of the present disclosure, a spinal correction system includes a tensioning member and a fulcrum tensioner device. The fulcrum tensioner device includes a housing defining a chamber having a biasing member therein and a divider operatively coupled with the biasing member. The divider defines a pair of slots configured to receive the tensioning member therethrough. The tensioning member is configured to be received in the biasing member and looped through the divider. The divider is transitionable between an extended position in which the biasing member applies tension to the tensioning member and a retracted position in which the biasing member is compressed.

In an embodiment, the housing may include a body and a flange extending radially outward from the body. The body may be configured to be received in a vertebral body.

In another embodiment, the divider may be biased towards the extended position.

In accordance with one aspect of the present disclosure, a spinal construct for correcting a spinal deformity includes first and second fixation members. The first fixation member is attachable to a first vertebra and the second fixation member is attachable to a second vertebra. The spinal construct also has a fulcrum tensioner device attachable to a third vertebra. The fulcrum tensioner device includes a housing, a biasing member disposed in the housing, and a camming pin operatively coupled with the biasing member. The camming pin is transitionable between an extended position and a retracted position. The spinal construct also has a tensioning member operatively coupled with the first fixation member, the second fixation member, and the fulcrum tensioner device. A first end of the tensioning member is securable to the first fixation member, a second end of the tensioning member is securable to the second fixation member, and an intermediate portion of the tensioning member is looped around the camming pin.

In embodiments, the fulcrum tensioner device may have a securing portion with a bore and the fulcrum tensioner device may be attachable to the third vertebra using a screw inserted through the bore.

In embodiments, the fulcrum tensioner device may further include a camming slot and a release tab. The release tab may be received in the camming slot to maintain the camming pin in the retracted position.

In embodiments, the first fixation member may be positioned on a first side of a spine and the second fixation member may be positioned on a second side of the spine opposite the first side.

In embodiments, the first fixation member, the second fixation member, and the fulcrum tensioner device are all positioned on one side of a spine.

In embodiments, the tensioning member wraps around a vertebra adjacent the first vertebra and wraps around a vertebra adjacent the second vertebra such that the tensioning member is positioned along both sides of the spine.

In embodiments, moving the first end of the tensioning member away from the fulcrum tensioner device imparts a first rotational force along the spine in a first direction.

In embodiments, moving the second end of the tensioning member from the fulcrum tensioner device imparts a second rotational force along the spine in a second direction opposite from the first direction.

In embodiment, the spinal construct may further include a tensioning instrument configured to apply tension to the tensioning member. The tensioning instrument may include a tensioning screw and a clamping mechanism. The clamping mechanism may include a clamp arm having a free position, in which the tensioning member may freely slide through the clamping mechanism, and a locked position, in which the tensioning member may be fixed relative to the clamping mechanism. The tensioning screw may move the clamping mechanism away from one of the first and second fixation members to apply tension to the tensioning member when the clamping mechanism is in the locked position. In accordance with another aspect of the present disclosure, a spinal correction method includes securing first and second fixation members to cranial and caudal vertebral bodies, securing a fulcrum tensioner device to a vertebral body interposed between the cranial and caudal vertebral bodies, inserting a portion of a tensioning member through a biasing member of the fulcrum tensioner device and looping around a camming pin operatively coupled with the biasing member to provide tension in the tensioning member, whereby a first end of the tensioning member is directed to a first direction and a second end of the tensioning member is directed to a second direction different from the first direction, wrapping a first end portion of the tensioning member around a first vertebral body adjacent the cranial vertebral body, wrapping a second end portion of the tensioning member around a second vertebral body adjacent the caudal vertebral body, securing the first end portion of the tensioning member with the first fixation member, and securing the second end portion of the tensioning member with the second fixation member.

In embodiments, securing the fulcrum tensioner device may include positioning the fulcrum tensioner device adjacent an inflection point of a spinal curvature.

In embodiments, securing the first end portion of the tensioning member may include extending at least a portion of the tensioning member through a cannulated shank of the first fixation member.

In embodiments, the method may further include placing a release tab within a camming slot defined in a housing of the fulcrum tensioner device to compress the biasing member to inhibit application of tension to the tensioning member.

BRIEF DESCRIPTION OF THE DRAWINGS

Various aspects of the present disclosure are described hereinbelow with reference to the drawings, wherein.

DETAILED DESCRIPTION

Figure 1:
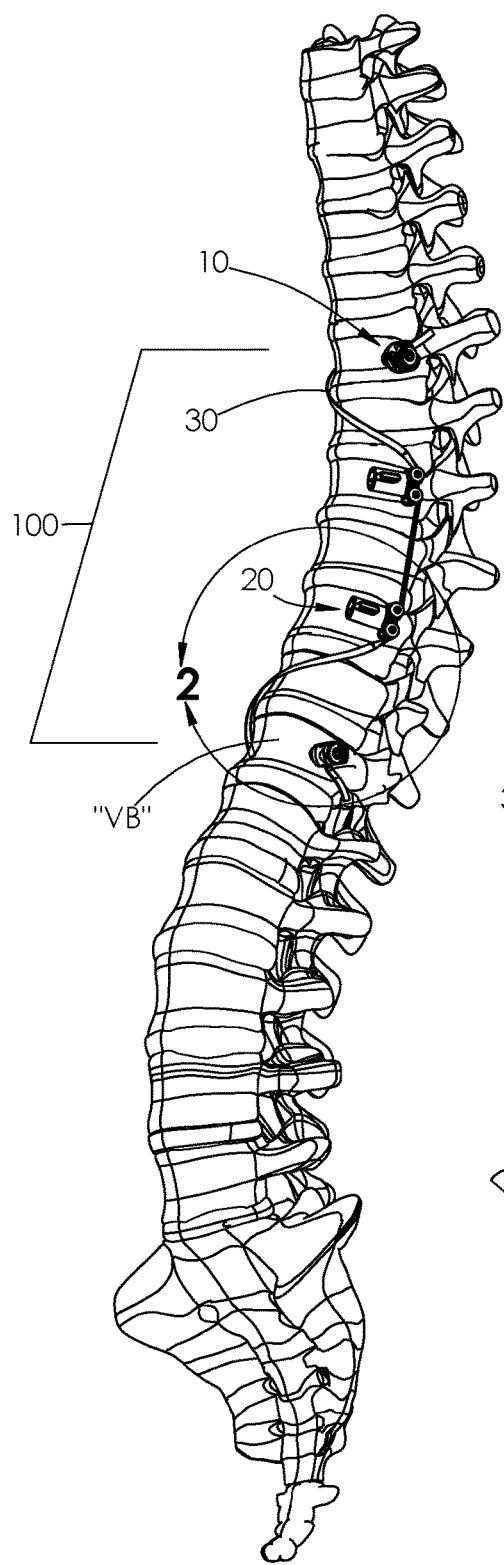
FIG. 1 is a perspective view of a spinal correction system in accordance with an embodiment of the present disclosure illustrating use on a spine.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" will refer to the portion of the device or component thereof that is closest to the clinician and the term "distal" will refer to the portion of the device or component thereof that is farthest from the clinician. In addition, the term "cephalad" is used in this application to indicate a direction toward a patient's head, whereas the term "caudad" indicates a direction toward the patient's feet. Further still, for the purposes of this application, the term "lateral" indicates a direction toward a side of the body of the patient, i.e., away from the middle of the body of the patient. The term "posterior" indicates a direction toward the patient's back, and the term "anterior" indicates a direction toward the patient's front. Additionally, in the drawings and in the description that follows, terms such as front, rear, upper, lower, top, bottom, and similar directional terms are used simply for convenience of description and are not intended to limit the disclosure.

Figure 2:
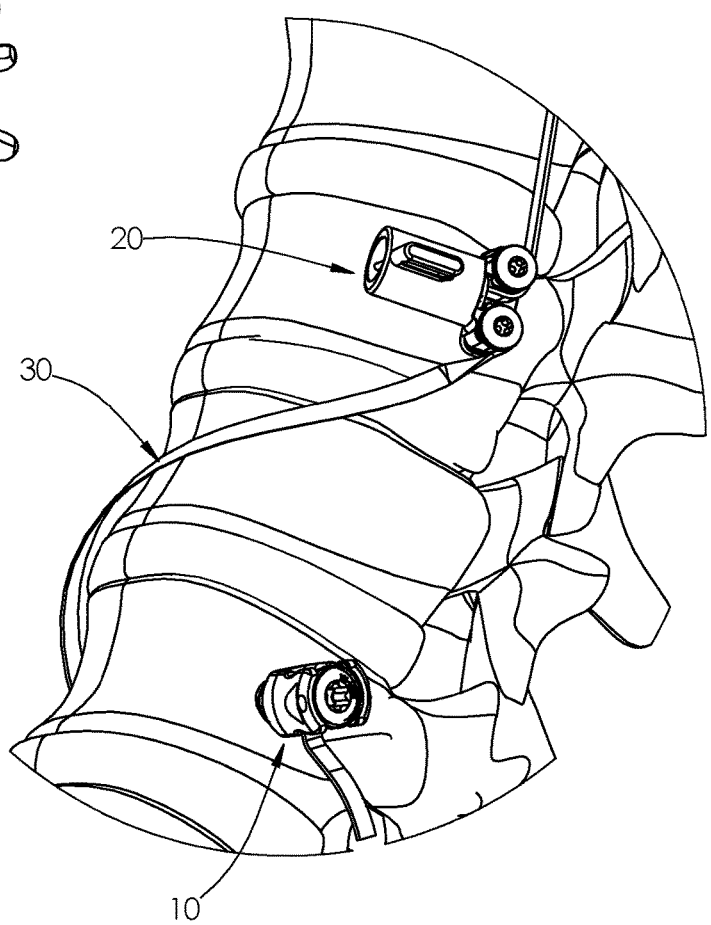
FIG. 2 is a perspective view of the area of detail indicated in FIG. 1.

With reference to FIGS. 1 and 2, a spinal correction system in accordance with an embodiment of the present disclosure is generally shown as a spinal correction system 100. Spinal correction system 100 may be utilized on, e.g., a scoliotic patient. Spinal correction system 100 may safely and reliably correct deformities of vertebral rotation and restore sagittal and coronal balance. Spinal correction system 100 includes a fixation member 10, a fulcrum tensioner device 20, and a tensioning member 30.

Figure 3:
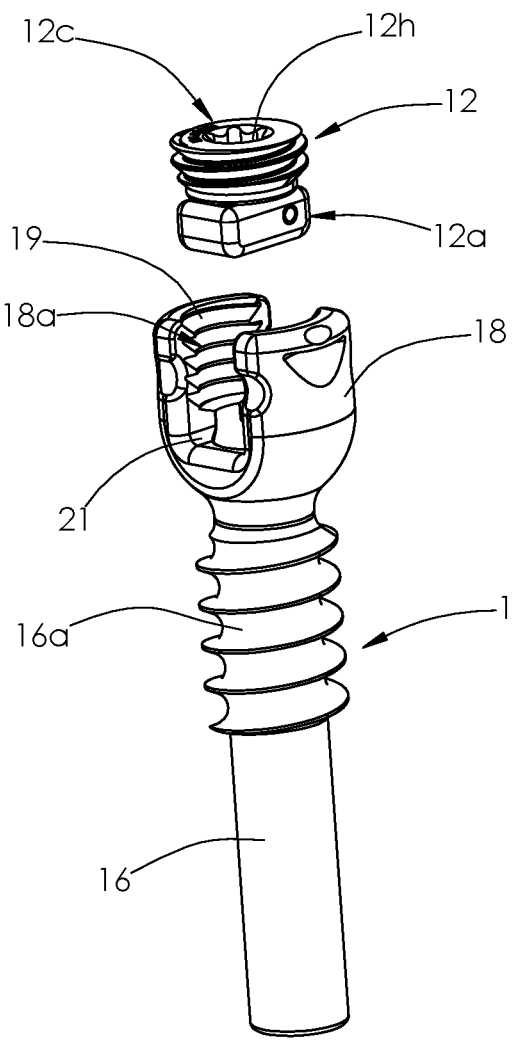
FIG. 3 is a perspective view of a fixation member of the spinal correction system of FIG. 1 with a set screw separated.
Figure 4:
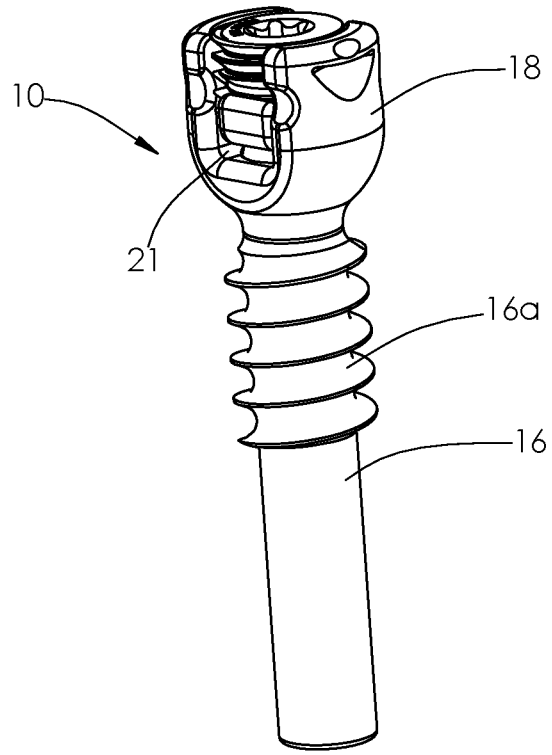
FIG. 4 is a perspective view of the fixation member of FIG. 3 with the set screw secured in a housing of the fixation member.

With reference to FIGS. 3 and 4, fixation member 10 may be, e.g., a cannulated monoaxial screw. In particular, fixation member 10 includes a head portion 18, a cannulated shank 16 extending distally from head portion 18, and a set screw 12. Cannulated shank 16 defines a passage 23 (FIG. 8) configured to receive at least a portion of tensioning member 30 therein. Cannulated shank 16 includes threads 16a configured to threadably engage bone. Head portion 18 defines a slot 21 configured to receive set screw 12. Slot 21 may define a U-shape configured to receive tensioning member 30 therethrough. An inner wall 19 of head portion 18 includes threads 18a configured to threadably engage set screw 12.

Figure 5:
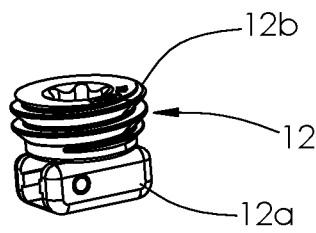
FIG. 5 is a perspective view of a set screw of the fixation member of FIG. 3.
Figure 6:
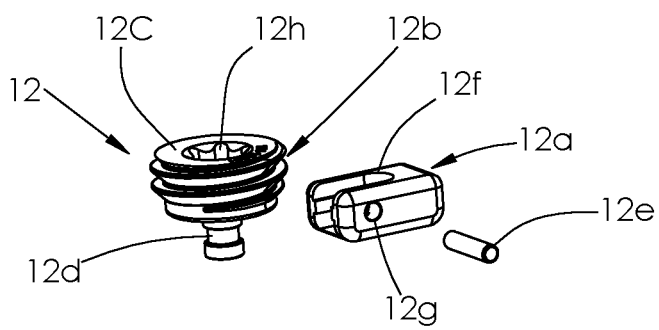
FIG. 6 is an exploded perspective view of the set screw of FIG. 5 with parts separated.

With reference to FIGS. 5 and 6, set screw 12 is utilized to secure tensioning member 30 with fixation member 10. Set screw 12 includes a base portion 12a and a threaded portion 12b configured to threadably engage threads 18a of head portion 18. Base portion 12a is rotatably coupled with threaded portion 12b. In particular, base portion defines a recess 12f configured to receive a neck portion 12d of threaded portion 12b. Base portion further defines a bore 12g dimensioned to receive a pin 12e configured to rotatably secure neck portion 12d of threaded portion 12b. In addition, base portion 12a may include a planar surface 12c (FIG. 8) configured to engage tensioning member 30. Under such a configuration, base portion 12a is positioned in slot 21 of head portion 18 and in contact with tensioning member 30. Base portion 12a maintains its orientation, while threaded portion 12b of set screw 12 is rotated to threadably secure set screw 12 with head portion 18. Set screw 12 includes a proximal portion 12c defining a cavity 12h having, e.g., a hex, key feature for non-slip engagement with a driver or other instrument (not shown) to drive set screw 12 into head portion 18. It is contemplated that cavity 12h may have any suitable configuration such as, e.g., slotted, square, star fitting, or a Phillips head, for engagement with the driver.

Figure 7:
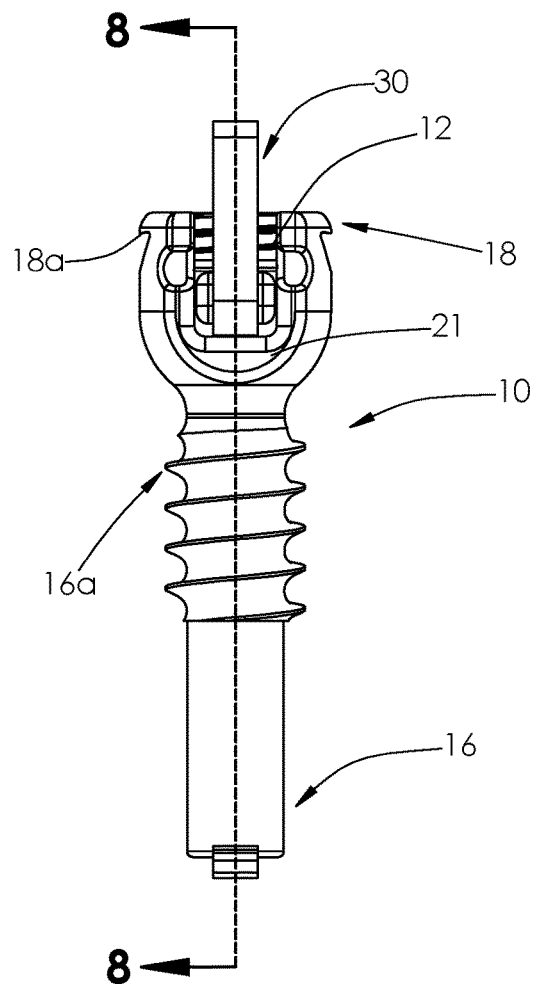
FIG. 7 is a side view of the fixation member of FIG. 3 with a tensioning member secured therewith.
Figure 8:
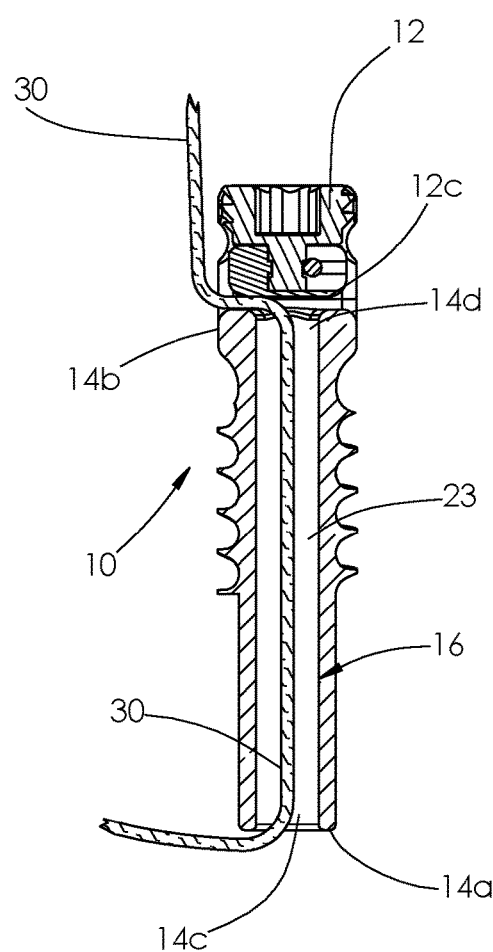
FIG. 8 is a side cross-sectional view of the fixation member of FIG. 7 taken along section line 8-8 of FIG. 7.
Figure 10:
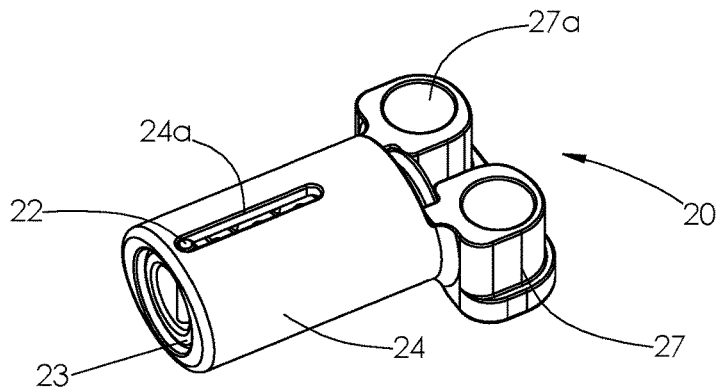
FIG. 10 is an exploded perspective view of the fulcrum tensioner device of FIG. 9 with parts separated.
Figure 9:
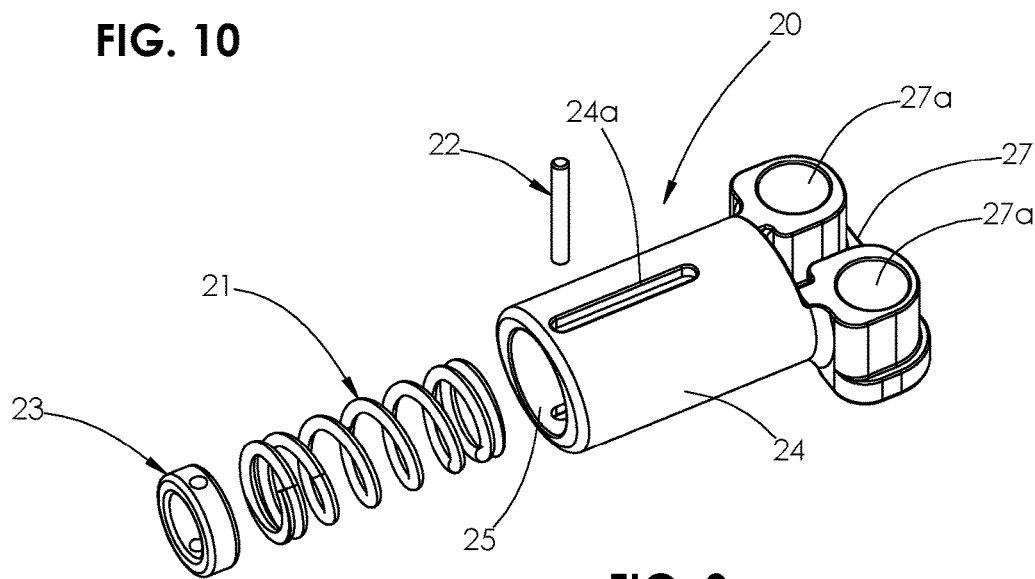
FIG. 9 is a perspective view of a fulcrum tensioner device of the spinal correction system of FIG. 1.
Figure 11:
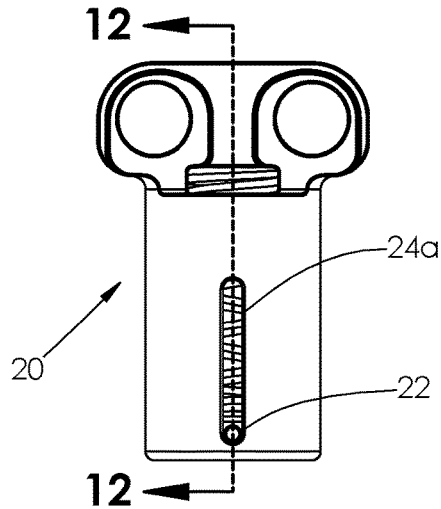
FIG. 11 is a top view of the fulcrum tensioner device of FIG. 9.
Figure 12:
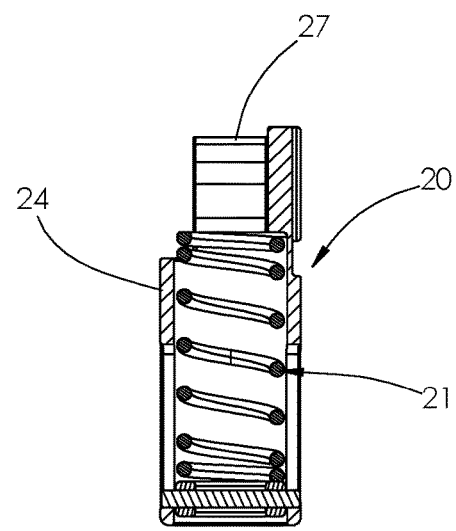
FIG. 12 is a side cross-sectional view of the fulcrum tensioner device of FIG. 11 taken along section line 12-12 of FIG. 11.

With reference now to FIGS. 7 and 8, cannulated shank 16 includes a distal end 14a defining a distal opening 14c and a proximal end 14b defining a proximal opening 14d. A first end of tensioning member 30 may extend through slot 21 of head portion 18 via proximal opening 14d. A second end of tensioning member 30 may extend through distal opening 14c. A portion of tensioning member 30 extending through proximal opening 14d is secured to proximal end 14b of cannulated shank 16 by set screw 12.

With reference now to FIGS. 9-12, fulcrum tensioner device 20 includes a housing 24 including a chamber 25 configured to receive a biasing member or spring 21. A cap 23 is used to retain spring 21 in chamber 25. Cap 23 includes a camming pin 22 configured to slidably engage slots or camming slots 24a defined in housing 24. Housing 24 further includes a securing portion 27 defining bores 27a dimensioned to receive bone anchors 26 (FIG. 13).

Figure 14:
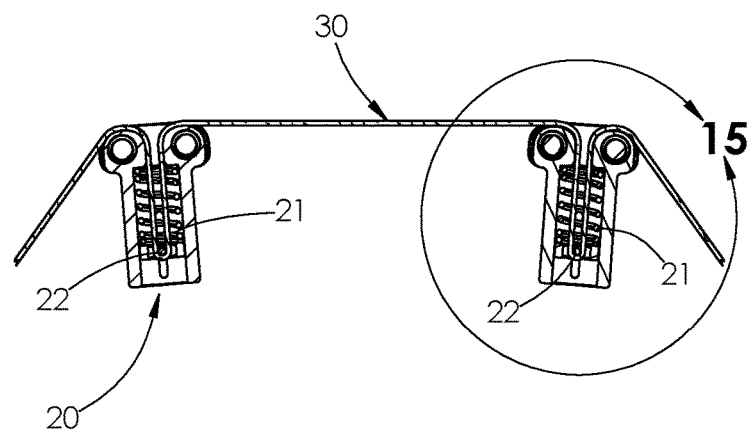
FIG. 14 is a cross-sectional view of the fulcrum tensioner devices of FIG. 11 taken along section line 14-14 of FIG. 13.
Figure 13:
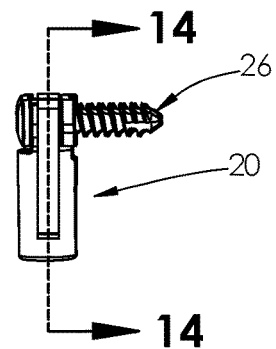
FIG. 13 is a side view of the fulcrum tensioner devices of FIG. 11 illustrating use with a screw.
Figure 15:
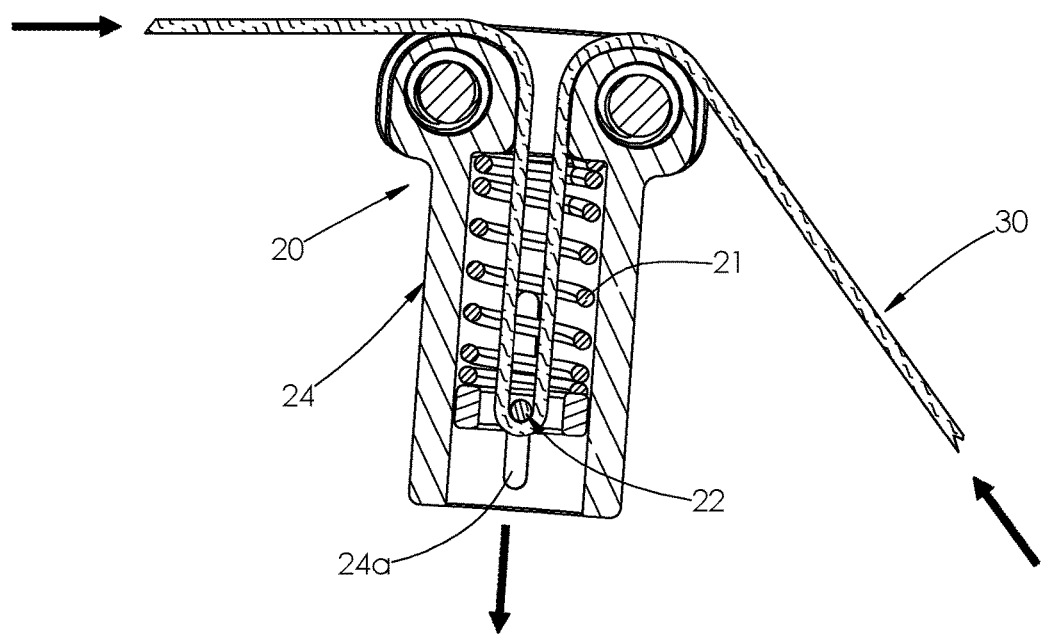
FIG. 15 is an enlarged cross-sectional view of the area of detail indicated in FIG. 14.
Figure 16:
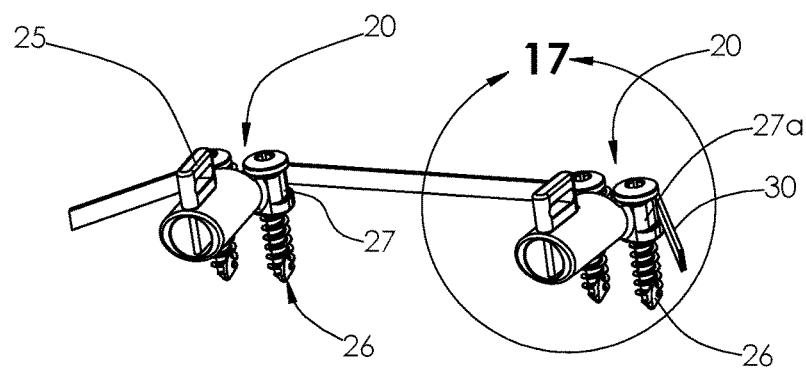
FIG. 16 is a perspective view of the fulcrum tensioner devices illustrating use with release tabs.
Figure 17:
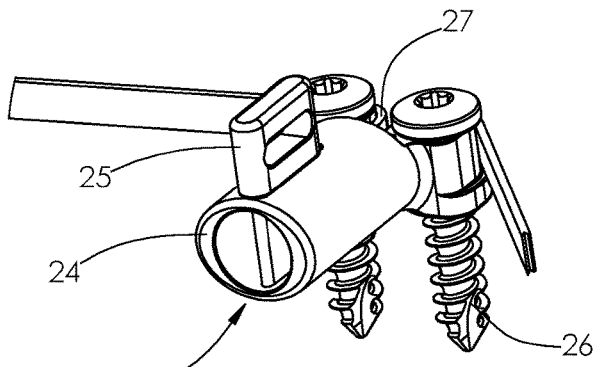
FIG. 17 is an enlarged perspective view of the area of detail indicated in FIG. 16.
Figure 18:
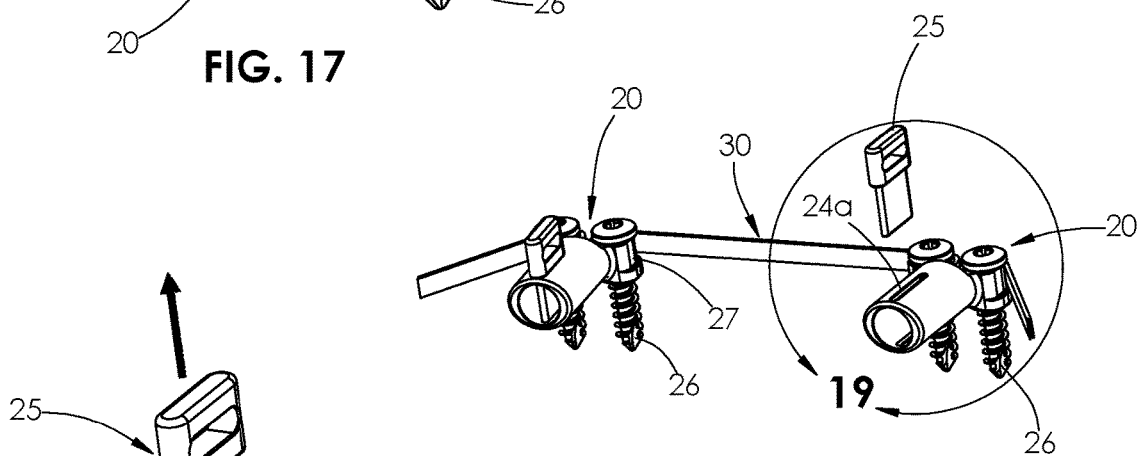
FIG. 18 is a perspective view of the fulcrum tensioner devices of FIG. 16 illustrating removable of the release tab.
Figure 19:
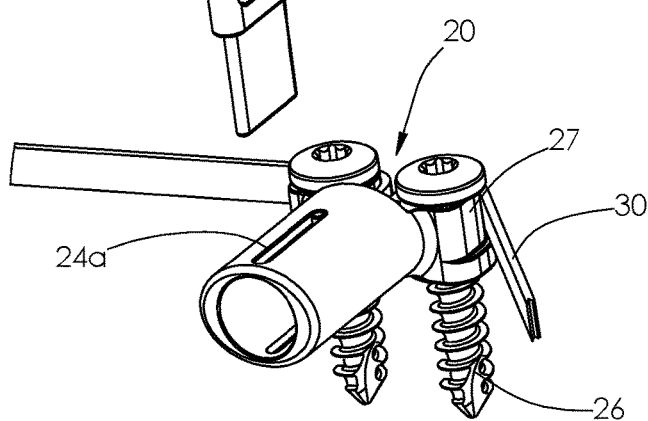
FIG. 19 is an enlarged perspective view of the area of detail indicated in FIG. 18.

With reference now to FIGS. 13-15, tensioning member 30 may be received through spring 21 disposed in chamber 25 of fulcrum tensioner device 20 and may be looped around pin 22. In this manner, the biasing force of spring 21 provides tension in tensioning member 30.

With reference now to FIGS. 16-19, fulcrum tensioner device 20 may further include a release tab 25 removably received in camming slot 24a of housing 24. When release tab 25 is placed in camming slot 24a, spring 21 is compressed and pin 22 is positioned closer to securing portion 27. Under such a configuration, release tab 25 positioned in camming slot 24a inhibits spring 21 from applying tension to tensioning member 30.

Tensioning member 30 may be, e.g., a flat, flexible tether. The flexible nature of tensioning member 30 may enable applications in various surgical procedures. With brief reference back to FIG. 1, tensioning member 30 may be wrapped around a vertebral body "VB". Tensioning member 30 may have a thickness that provides a desired amount of flexibility or malleability for a selected application. The material of construction, e.g., polymeric or metallic, may be selectively chosen to provide the desired amount of flexibility. Tensioning member 30 may have a flat rectangular cross-section that enables, e.g., a surface contact, with set screw 12 (FIG. 8). For example, tensioning member 30 may be dimensioned to be received in groove 27a (FIG. 16) of securing portion 27 to facilitate or guide placement of tensioning member 30 around securing portion 27.

It is contemplated that tensioning member 30 may include a guide wire, e.g., embedded therein. The guide wire may be a stiffening wire to increase the stiffness of tensioning member 30. The stiffening wire may be embedded in tensioning member 30 or may be externally bonded (i.e., bonded on an external surface of the body). The stiffening wire may be bonded along the entire length of the body or only a portion of the length of the body. Reference may be made to U.S. Patent Application Publication No. 2014/0257397, filed on Mar. 11, 2014, entitled "Flexible Fastening System," the entire content of which is incorporated herein by reference, for a detailed discussion of the construction and operation of the fastening system.

Tensioning member may be, e.g., a spring or a band. Tensioning member 30 may be made from various polymers including, e.g., nylon, Dacron®, Ultra-High-Molecular-Weight Polyethylene (UHMWPE), polypropylene, polyester, polyether ether ketone (PEEK), polyphenylsulfone (PPSU), polyetherimide (PEI), polyacetal, or any combinations thereof. It is also envisioned that tensioning member 30 may be formed from stainless steel, titanium, titanium alloys, cobalt chrome, nitinol, and other suitable biocompatible materials.

Figure 20:
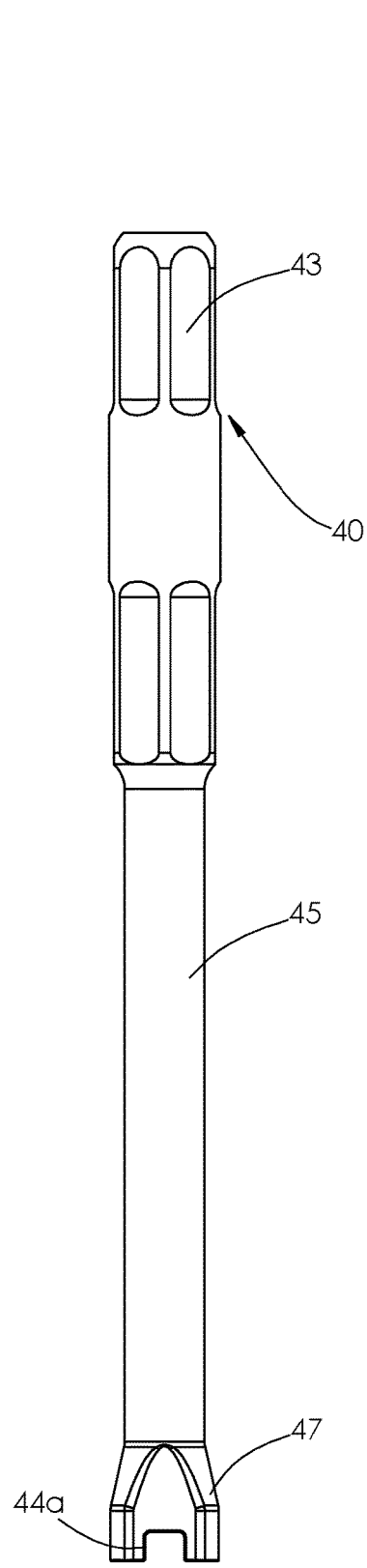
FIG. 20 is a front view of an insertion instrument for use with the fixation member of FIG. 3.
Figure 21:
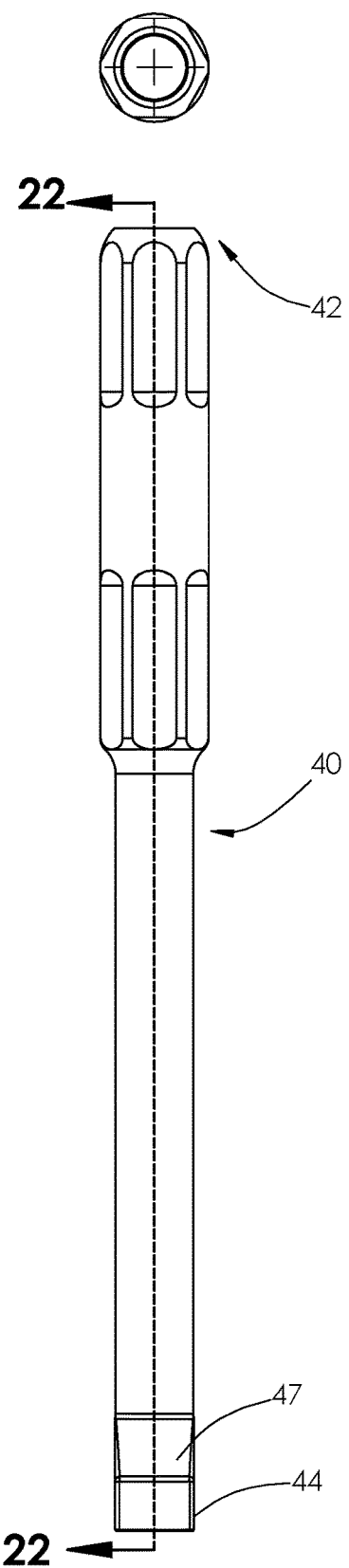
FIG. 21 is a side view of the insertion instrument of FIG. 20.
Figure 22:
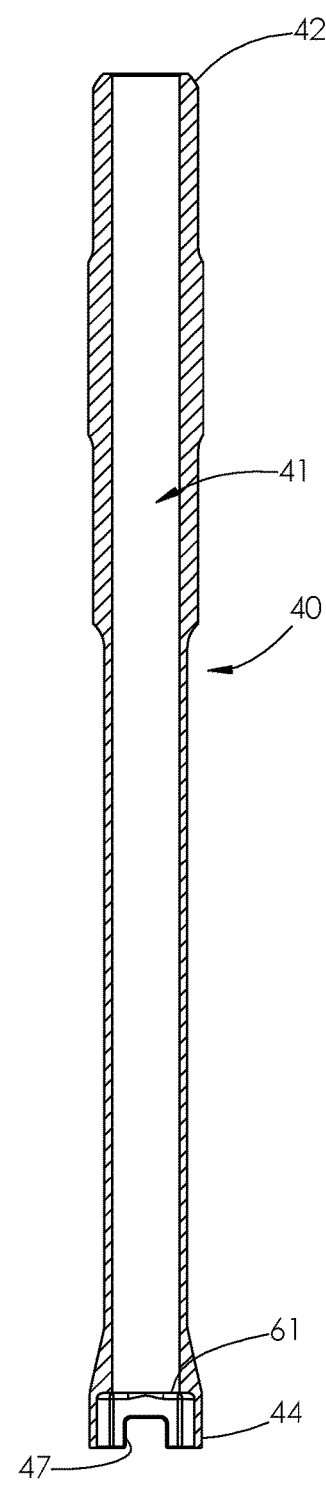
FIG. 22 is a side cross-sectional view of the insertion instrument of FIG. 21 taken along section line 22-22 of FIG. 21.

With reference now to FIGS. 20-22, spinal correction system 100 may further include an insertion instrument 40 configured to insert fixation member 10 to the surgical site of interest. For example, insertion instrument 40 may be used to insert fixation member 10, e.g., laterally to obtain bi-cortical fixation of fixation member 10. Insertion instrument 40 includes a handle 43, a shaft 45 extending from handle 40, and an engaging portion 47 attached to a distal end of shaft 45. Engaging portion 47 defines a groove 61 configured to detachably receive a lip 18a (FIG. 7) of head portion 18 of fixation member 10. Engaging portion 47 may include, e.g., a snap fit, configuration. Engaging portion 47 further defines a notch 44a dimensioned to receive tensioning member 30 therethrough.

With continued reference to FIGS. 20-22, insertion instrument 40 may define a passage 41 extending between proximal and distal ends 42, 44 of insertion instrument 40. Passage 41 may be dimensioned to receive set screw 12 such that set screw 12 may be positioned in slot 21 of head portion 18 of fixation device 10, while head portion 18 is detachably connected to engaging portion 47. In this manner, the use of insertion instrument 40 may facilitate alignment of threaded portion 12b of set screw 12 with threads 18 a on inner wall 19 of fixation member 10.

Figure 26:
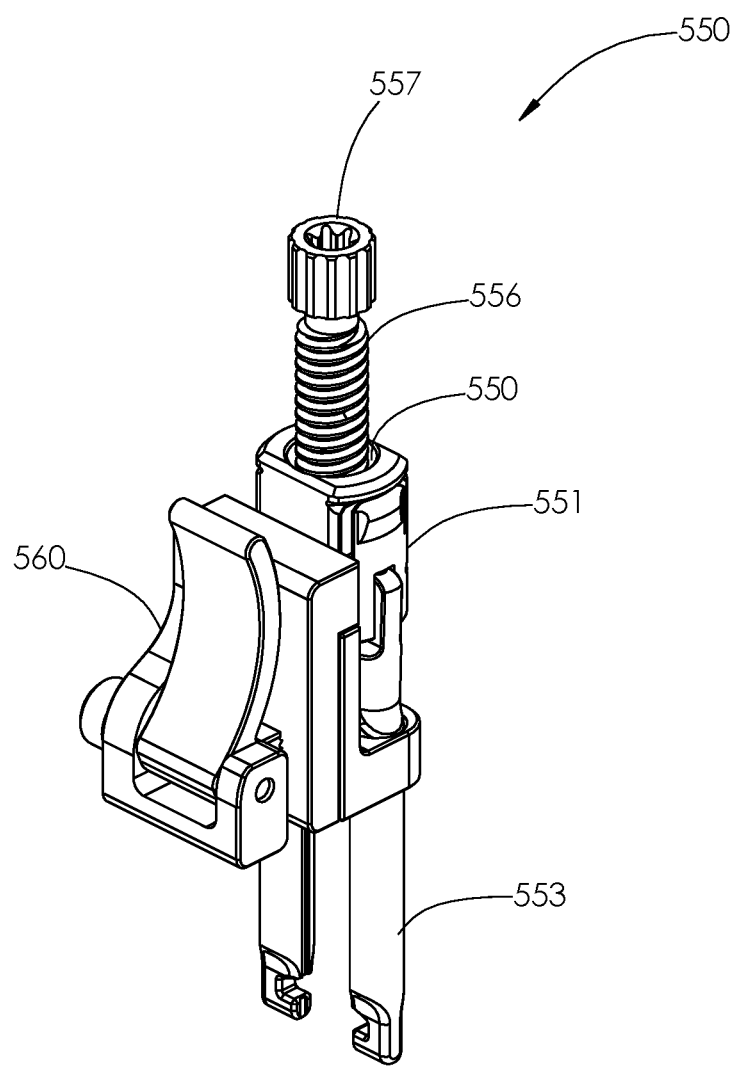
FIG. 26 is a perspective view of a tensioning instrument for use with the spinal correction system of FIG. 1.
Figure 27:
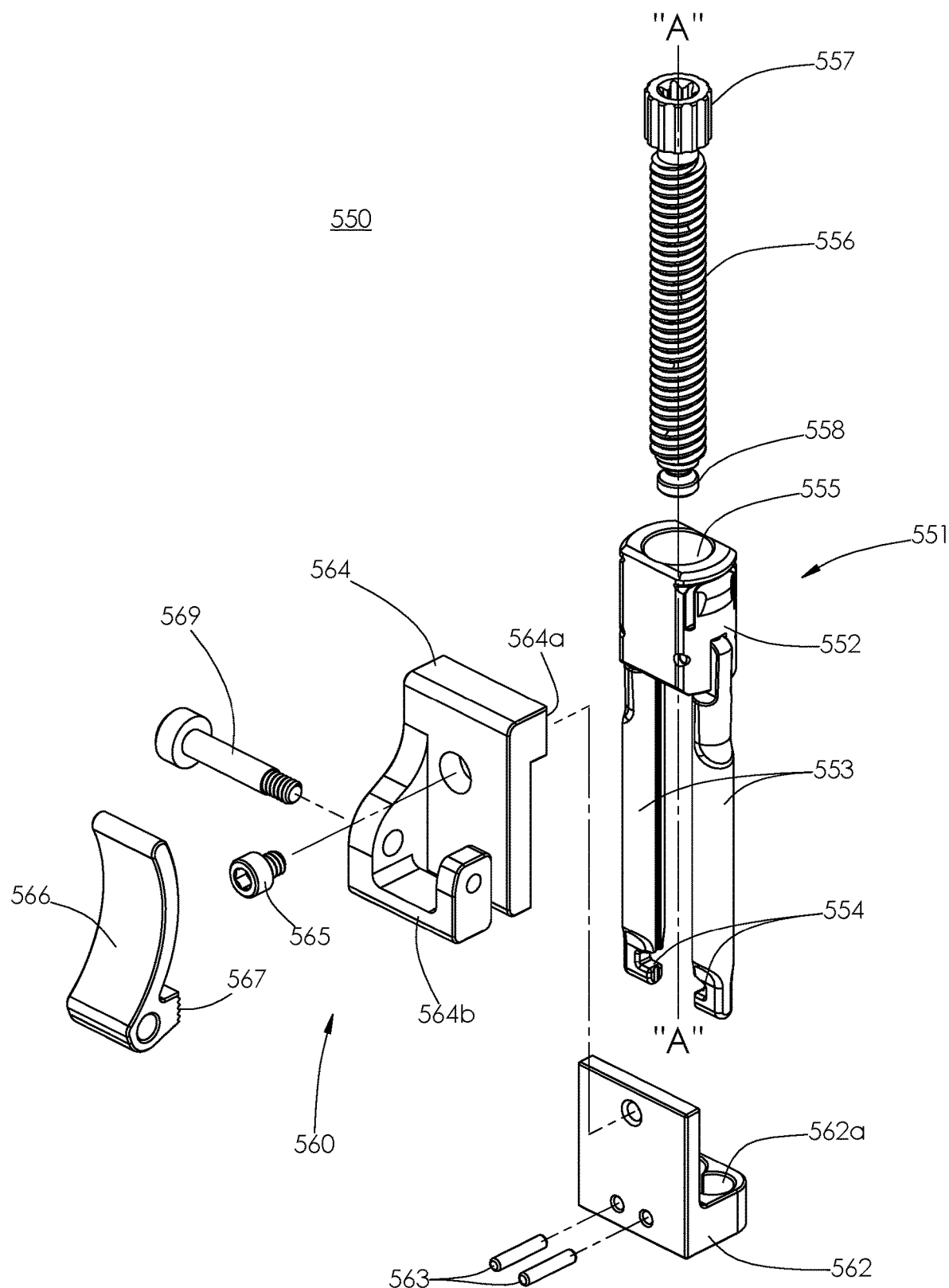
FIG. 27 is an exploded perspective view of the tensioning instrument of FIG. 26 with parts separated.
Figure 28:
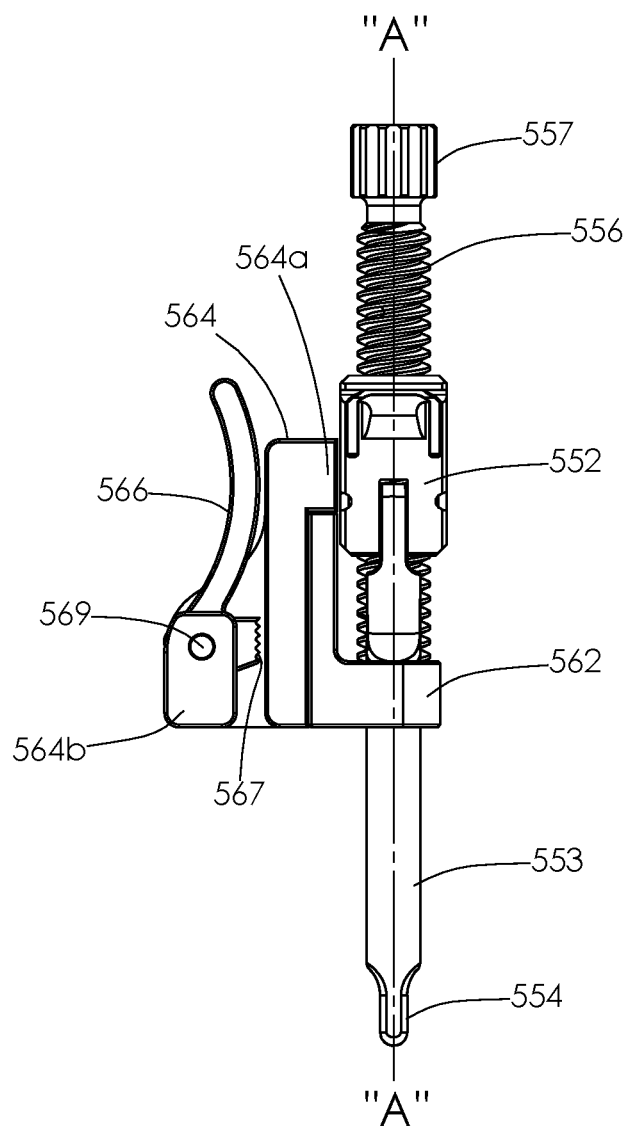
FIG. 28 is a side view of the tensioning instrument of FIG. 26.

With reference now to FIGS. 26-28, spinal correction system 100 may include a tensioning instrument 550 configured to apply tension to tensioning member 30 (FIG. 1) coupled with fixation member 10 (FIG. 1). Tensioning instrument 550 includes a tensioning mechanism 551 and a clamping mechanism 560. Tensioning mechanism 551 includes a tensioning body 552 defining a longitudinal axis "A-A." Tensioning body 552 includes arms 553 extending parallel to the longitudinal axis "A-A." Arms 553 terminate in fingers 554 that are configured to engage a portion of head portion 18 (FIG. 3) of fixation member 10. Arms 553 may be pivotable towards and away from longitudinal axis "A-A". Arms 553 are pivoted away from longitudinal axis "A-A" and out of the parallel arrangement to engage head portion 18 of fixation member 10 and are pivoted towards longitudinal axis "A-A" into the parallel arrangement when engaged with head portion 18. Tensioning body 552 further defines a threaded hole 555 along longitudinal axis "A-A." Threaded hole 555 receives a tensioning screw 556. Tensioning screw 556 includes a head 557 adjacent a proximal end thereof and a tensioning disc 558 adjacent a distal end thereof.

With particular reference to FIG. 27, clamping mechanism 560 includes a receiver 562, a clamp base 564, and a clamp arm 566. Receiver 562 defines openings 562a sized to permit the arms 553 to pass through the receiver 562. A pair of disc pins 563 is received within receiver 562 about tensioning screw 556 such that tensioning screw 556 is retained within threaded hole 555 and fixed relative to receiver 562. Clamp base 564 is coupled to receiver 562 by a base screw 565. Clamp base 564 may include a protrusion 564a configured to align clamp base 564 with receiver 562. Clamp base 564 includes an arm mount 564b configured to pivotally retain clamp arm 566. A pivot screw 569 passes through arm mount 564b and clamp arm 566 to retain clamp arm 566 to clamp base 564. Clamp arm 566 includes an engagement portion 567 to capture tensioning member 30 between clamp arm 566 and clamp base 564.

In use, fingers 554 of arms 553 engage head portion 18 of fixation member 10 (FIG. 3) to longitudinally fix tensioning body 552 relative to fixation member 10. A portion of tensioning member 30 is passed through passage 23 (FIG. 8) and distal opening 14c of cannulated shank 16 and out of slot 21 (FIG. 7) of head portion 18. Thereafter, the portion of tensioning member 30 is passed between clamp arm 566 and clamp base 564 with clamp arm 566 in a free position, in which tensioning member 30 is freely slidable between clamp base 564 and clamp arm 566. Tensioning screw 556 is rotated until receiver 562 is adjacent head portion 18 and head 557 is adjacent tensioning body 552.

When head 557 of tensioning screw 556 is adjacent tensioning body 552, the portion of tensioning member 30 is held or partially tensioned as clamp arm 566 is moved to the clamped position, in which engagement portion 567 captures tensioning member 30 disposed between clamp arm 566 and clamp base 564 to inhibit tensioning member 30 from moving relative to head portion 18 of fixation member 10. With clamp arm 566 in the clamped position, tensioning screw 556 is rotated within tensioning body 552 to move clamping mechanism 560 away from head portion 18 of fixation member 10. Tensioning disc 558 of tensioning screw 556 is fixed relative to receiver 562 to move receiver 562 away from fixation member 10. As receiver 562 moves away from fixation member 10, clamp base 564 moves away from fixation member 10 to apply tension to tensioning member 30 that is captured by clamp arm 566 and fixed relative to clamp base 564. When tension is applied to tensioning member 30, set screw 12 (FIG. 8) may be used to fix tensioning member 30 to fixation member 10. When tensioning member 30 is fixed to fixation member 10, tensioning instrument 550 may be removed from fixation member 10. Reference may be made to U.S. Patent Application Publication No. 2014/0257397, filed on Mar. 11, 2014, entitled "Flexible Fastening System," the entire content of which is incorporated herein by reference, for a detailed discussion tensioning instrument 550.

Figure 23:
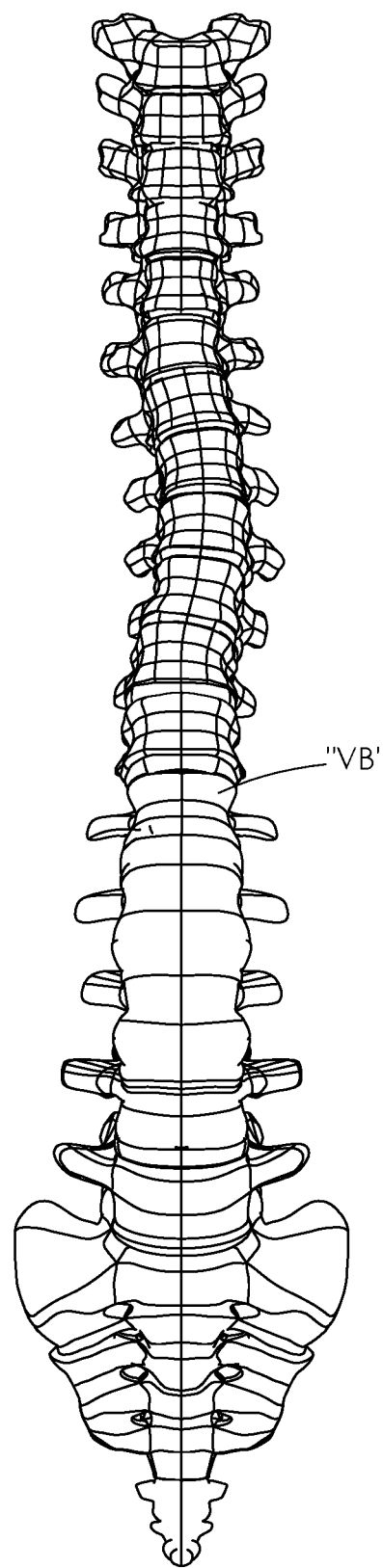
FIGS. 23-25 are perspective views of the spinal correction system of FIG. 1 illustrating use thereof on a spine.
Figure 24:
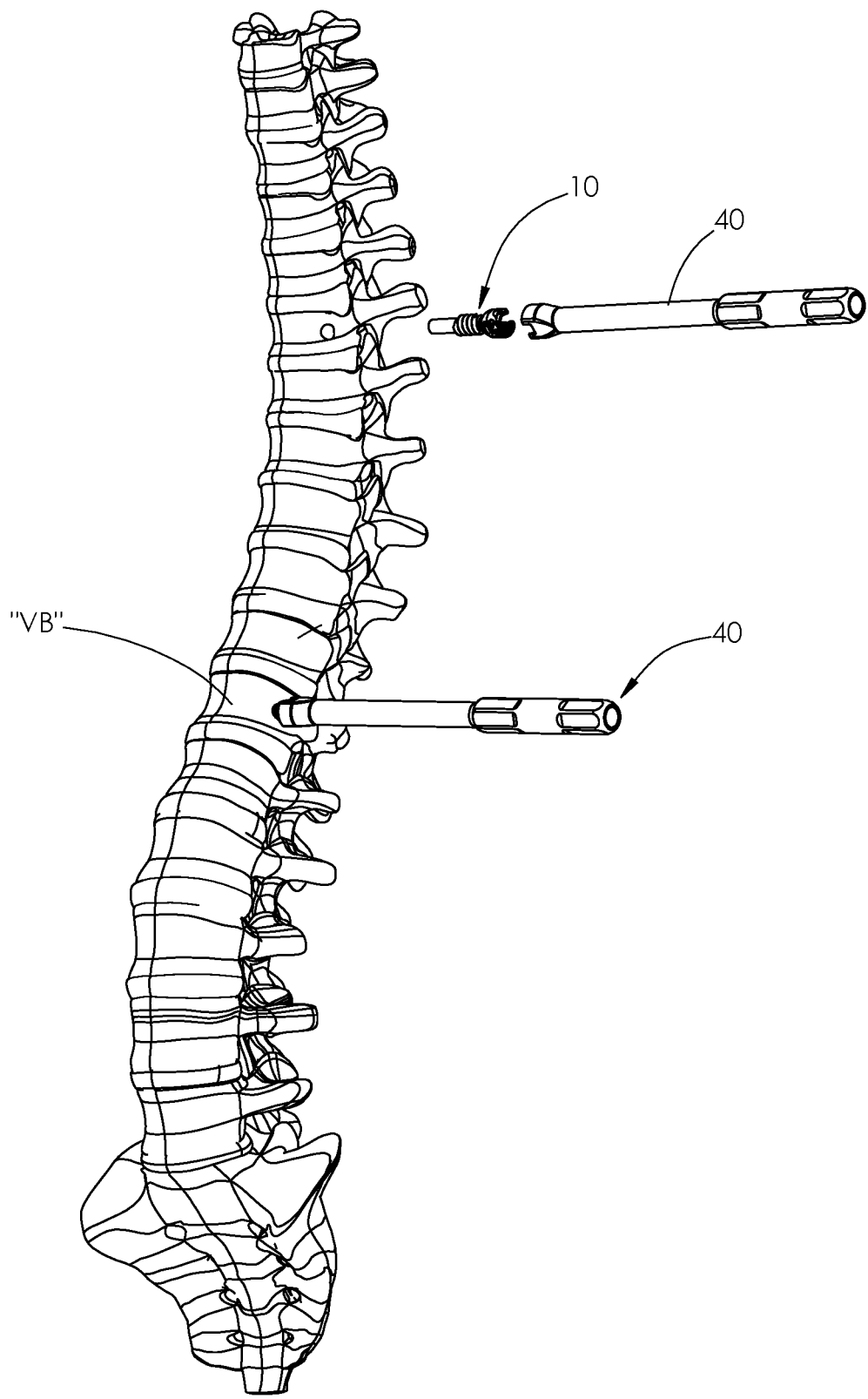
Figure 25:
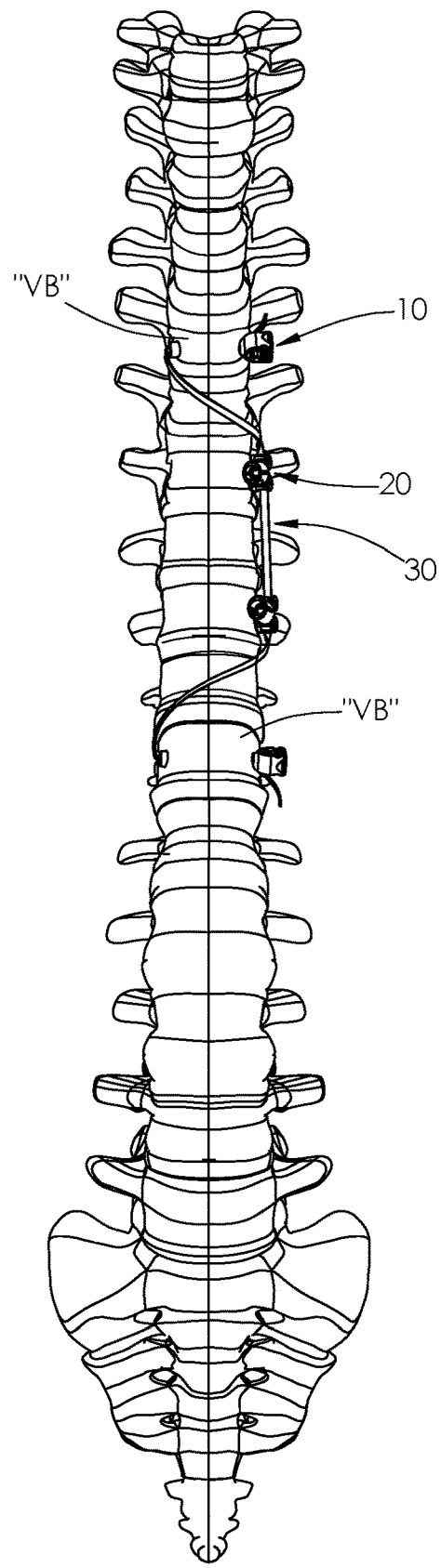

With reference now to FIGS. 23-25, in use the clinician may initially perform various spinal procedures including a thoracotomy, e.g., on the convex side of the spinal deformity. The clinician may determine the degree of correction needed for the spinal deformity (FIG. 23) of the particular patient and select the optimal placement of spinal correction system 100. Fixation members 10 may be placed, e.g., bi-cortically, into two or more vertebral bodies "VB" using insertion instrument 40. A first fixation member 10 may be affixed to a cranial vertebral body "VB" and a second fixation member 10 may be affixed to a caudal vertebral body "VB."

A number of fulcrum tensioner devices 20 may be selected based on the desired amount of tension applied to tensioning member 30. Fulcrum tensioner devices 20 may be affixed to vertebral bodies "VB" at or adjacent, e.g., the apex of the spinal curve or inflection points. Fulcrum tensioner devices 20 are affixed to vertebral bodies "VB" with the use of screws 26. Tensioning member 30 may be placed through spring 21 disposed in chamber 25 of fulcrum tensioner device 20 and looped around pin 22 prior to or during the procedure.

A first end portion of tensioning member 30 may be wrapped around a vertebral body "VB" adjacent cranial vertebral body "VB" having the first fixation member 10 affixed thereto and thereafter inserted into passage 23 (FIG. 8) of cannulated shank 16 of the first fixation member 10. At this time, tensioning instrument 550 may be used on the first fixation member 10 to apply tension to tensioning member 30. Set screw 12 is utilized to secure tensioning member 30 with the first fixation member 10. Similarly, a second end of tensioning member 30 is wrapped around a vertebral body "VB" adjacent caudal vertebral body "VB" having the second fixation member 10 affixed thereto and thereafter inserted into passage 23 of cannulated shank 16 of the second fixation member 10. At this time, tensioning instrument 550 may be used on the second fixation member 10 to apply tension to tensioning member 30. Set screw 12 is utilized to secure tensioning member 30 to the second fixation member 10.

Once tensioning member 30 is properly affixed to vertebral bodies "VB" via fixation members 10 and fulcrum tensioner devices 20, release tab 25 may be removed from camming slot 24a of housing 24 of fulcrum tensioner devices 20 to apply tension to tensioning member 30 for desired correction or re-alignment of the spine. Thereafter, tensioning member 30 may further be manipulated to provide, e.g., proper alignment or tension, with respect to vertebral bodies "VB". To this end, release tab 25 may be re-inserted into camming slots 24a (FIG. 19) of fulcrum tensioner device 20 to inhibit application of tension to tensioning member 30 by spring 21 in order to facilitate re-adjustment of fixation member 10 and/or fulcrum tensioner devices 20.

Figures 29A, 29B:
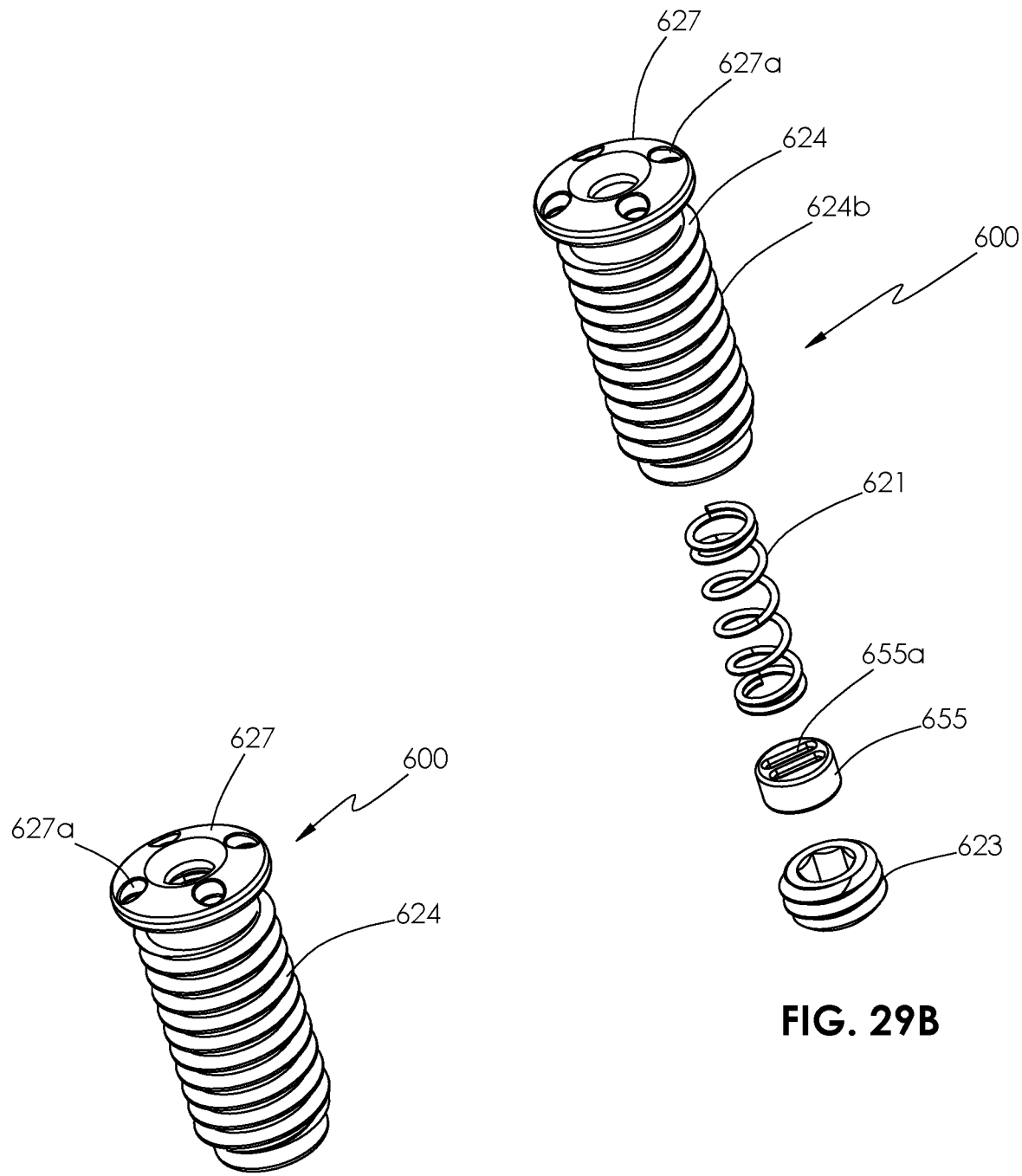
FIG. 29A is a perspective view of a fulcrum tensioner device in accordance with another embodiment of the present disclosure.
FIG. 29B is an exploded perspective view of the fulcrum tensioner device of FIG. 29A with parts separated.

With reference now to FIGS. 29A and 29B, a fulcrum tensioner device in accordance with another embodiment of the present disclosure is generally shown as a fulcrum tensioner device 600 configured to be embedded in vertebral body "VB" such that fulcrum tensioner device 600 provides a reduced profile. Fulcrum tensioner device 600 includes a housing 624 defining a chamber 625 (FIG. 32) configured to receive a biasing member or spring 621, a divider 655, and a cap 623. Divider 655 defines a pair of slits 655a configured to receive tensioning member 30 therethrough such that tensioning member 30 is looped through slots or openings in divider 655. Cap 623 is used to retain spring 621 and divider 655 in chamber 625. In particular, cap 623 may be threadably coupled to an inner wall 624a (FIG. 32) of chamber 625. Spring 621 is positioned between a surface of cap 623 and a shoulder defined at an opposed end of chamber 625. Housing 624 further includes a flange portion 627 defining bores 627a dimensioned to engage a driver instrument (not shown) to drive fulcrum tensioner device 600 into vertebral body "VB."

Figure 30:
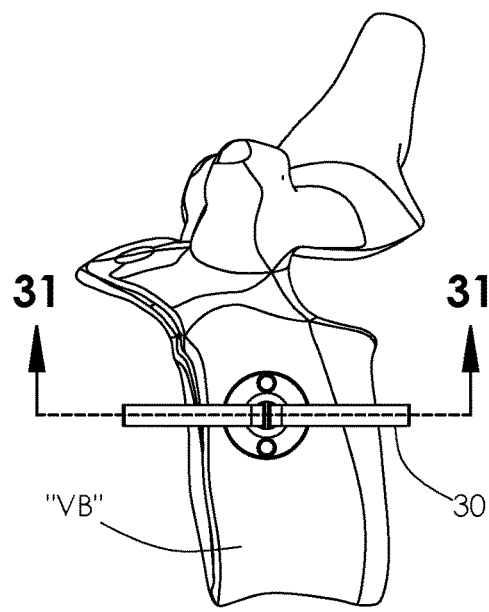
FIG. 30 is a top view of the fulcrum tensioner device of FIG. 29A illustrating the tensioning member inserted through the fulcrum tensioner device affixed to a vertebral body.
Figure 31:
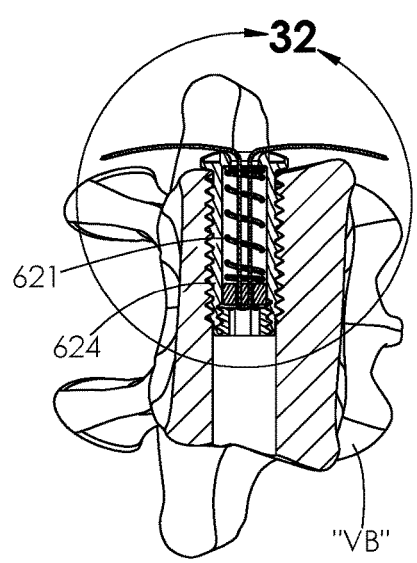
FIG. 31 is a side cross-sectional view of the fulcrum tensioner device of FIG. 30.
Figure 32:
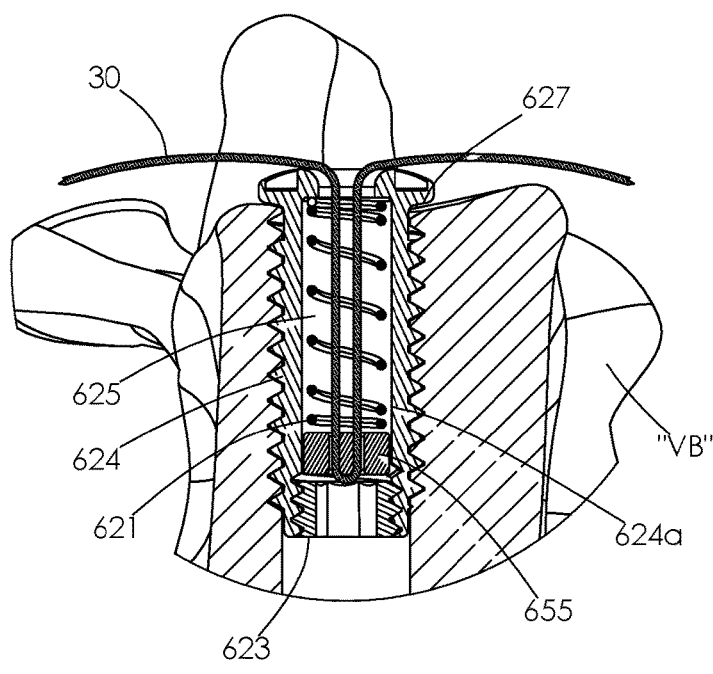
FIG. 32 is an enlarged side cross-sectional view of the area of detail indicated in FIG. 31.

With reference now to FIGS. 30-32, housing 624 of fulcrum tensioner device 600 includes threads 624b (FIG. 29B) configured to engage vertebral body "VB." Flange portion 627 extends radially outward from housing 624 such that flange portion 627 inhibits complete insertion of fulcrum tensioner device 600 in vertebral body "VB." Flange portion 627 has a reduced profile such that when fulcrum tensioner device 600 is received in vertebral body "VB," flange portion 627 is substantially flush with vertebral body "VB."

With particular reference to FIG. 32, tensioning member 30 may be received through spring 621 disposed in chamber 625 of fulcrum tensioner device 600 and may be looped through divider 655. In this manner, the biasing force of spring 621 provides tension in tensioning member 30 due to the biasing force of spring 621 being applied to divider 655.

Figure 33:
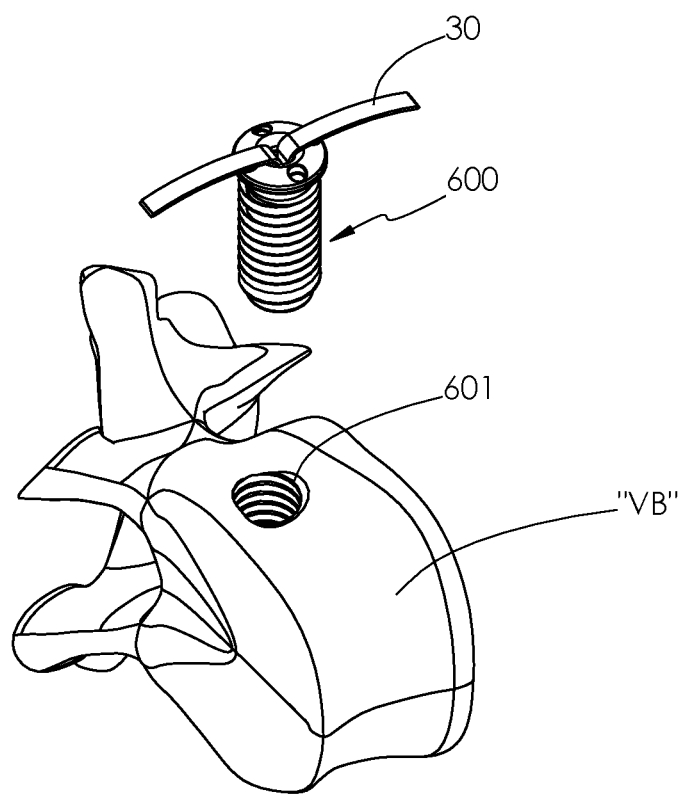
FIGS. 33 and 34 are perspective views of the fulcrum tensioner device of FIG. 29A illustrating use thereof with a vertebral body.
Figure 34:
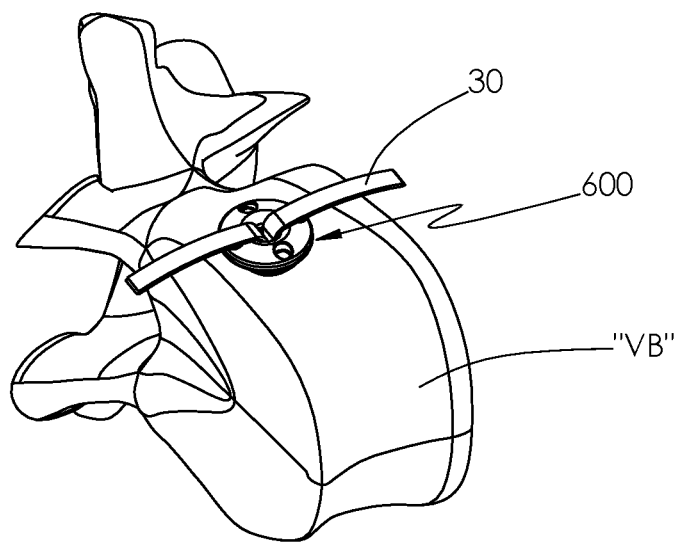

With reference now to FIGS. 33 and 34, a pre-drilled bore 601 in vertebral body "VB" may facilitate the insertion process of fulcrum tensioner device 600 into vertebral body "VB." The method of use of fulcrum tensioner device 600 is substantially identical to the method of use described hereinabove with respect to fulcrum tensioner device 20, and thus will not be described herein.

While the use of spinal correction system 100 has been described with vertebral bodies "VB," it is contemplated that spinal correction system 100 may be use with other bony elements in a patient. It is within the scope of the present disclosure that a plurality of spinal correction systems 100 may be used to provide a plurality of mounting points along a bony element of a patient's anatomy. It is also contemplated that tensioning member 30 may be coupled to a plurality of fixation member 10 and fulcrum tensioner devices 20 without looping around a bony element.

It is also envisioned that the presently disclosed spinal correction system 100 may be used with one or more spinal staples. The spinal staples may have barbs or other engaging structures on a surface of the spinal staple for positive engagement with the bone while inhibiting relative displacement between the spinal staple and the bone. An example of a spinal staple is described in U.S. Patent Application Publication No. 2010/0094358, filed on Oct. 13, 2009, the entire contents of which is incorporated herein by reference. Additionally, spinal correction system 100 may include a bone screw with barbs or other retention structures located on a distal surface of the bone screw for positive engagement with the bone while inhibiting relative movement between the bone screw and the bone.

While several embodiments of the disclosure have been shown in the drawings, it is not intended that the disclosure be limited thereto, as it is intended that the disclosure be as broad in scope as the art will allow and that the specification be read likewise. For example, fixation member 10 may be a cannulated monoaxial hook. Any combination of the above embodiments is also envisioned and is within the scope of the appended claims. Therefore, the above description should not be construed as limiting, but merely as exemplifications of particular embodiments. Those skilled in the art will envision other modifications within the scope and spirit of the claims appended hereto.

What is claimed is:

1. A spinal correction system comprising:
    a tensioning member; and
    a fulcrum tensioner device including:
        a housing defining a chamber having a biasing member therein;
        a camming pin operatively coupled with the biasing member, the tensioning member configured to be received in the biasing member and looped around the camming pin such that a first end of the tensioning member is oriented in a first direction and a second end of the tensioning member is oriented in a second direction, wherein the camming pin is transitionable between an extended position in which the biasing member applies tension to the tensioning member and a retracted position in which the biasing member is compressed to inhibit application of tension to the tensioning member; and
        a securing portion defining a bore configured to receive a screw to secure the fulcrum tensioner device to a vertebral body.

2. The spinal correction system according to claim 1, wherein the housing defines a longitudinal axis and a slot extending along the longitudinal axis, the slot configured to slidably receive the camming pin.

3. The spinal correction system according to claim 1, wherein the fulcrum tensioner device further includes a cap defining a bore dimensioned to receive the camming pin, the cap configured to retain the biasing member within the chamber of the housing.

4. The spinal correction system according to claim 1, wherein the camming pin is biased towards the extended position.

5. The spinal correction system according to claim 1, further including a fixation member including a cannulated screw defining a passage dimensioned to receive the tensioning member.

6. The spinal correction system according to claim 5, wherein the cannulated screw includes a housing and a shaft extending distally from the housing, the housing including a recess dimensioned to receive the tensioning member.

7. The spinal correction system according to claim 6, wherein the fixation member further includes a set screw having a base portion and a threaded portion rotatably coupled with the base portion, the threaded portion configured to threadably engage an inner surface of the housing of the cannulated screw.

8. The spinal correction system according to claim 7, wherein the base portion includes a planar surface adapted to engage the tensioning member.

9. The spinal correction system according to claim 7, wherein the base portion has a non-circular cross-section to inhibit rotation of the base portion when disposed in the housing of the cannulated screw.

10. The spinal correction system according to claim 1, wherein the securing portion defines a groove configured to guide the tensioning member.

11. The spinal correction system according to claim 1, wherein the fulcrum tensioner device further includes a release tab dimensioned to be detachably received in the camming slot to maintain the camming pin in the retracted position.

12. The spinal correction system according to claim 1, wherein the securing portion includes a screw configured to secure the fulcrum tensioner device to a vertebral body.

13. The spinal correction system according to claim 1, wherein the tensioning member is formed of a flexible material.

14. A spinal construct for correcting a spinal deformity, the spinal construct comprising:
    first and second fixation members, the first fixation member attachable to a first vertebra and the second fixation member attachable to a second vertebra;
    a fulcrum tensioner device attachable to a third vertebra, the fulcrum tensioner device including:
        a housing,
        a biasing member disposed in the housing, and
        a camming pin operatively coupled with the biasing member and transitionable between an extended position and a retracted position;
    a tensioning member operatively coupled with the first fixation member, the second fixation member, and the fulcrum tensioner device, a first end of the tensioning member securable to the first fixation member, a second end of the tensioning member securable to the second fixation member, and an intermediate portion of the tensioning member looped around the camming pin; and
    a securing portion with a bore and is attachable to the third vertebra using a screw inserted through the bore.

15. The spinal construct of claim 14, wherein the fulcrum tensioner device further includes a camming slot and a release tab, the release tab received in the camming slot to maintain the camming pin in the retracted position.

16. The spinal construct of claim 14, wherein the first fixation member is positioned on a first side of a spine and the second fixation member is positioned on a second side of the spine opposite the first side.

17. The spinal construct of claim 14, wherein the first fixation member, the second fixation member, and the fulcrum tensioner device are all positioned on one side of a spine.

18. The spinal construct of claim 17, wherein the tensioning member wraps around a vertebra adjacent the first vertebra and wraps around a vertebra adjacent the second vertebra such that the tensioning member is positioned along both sides of the spine.

19. The spinal construct of claim 18, wherein moving the first end of the tensioning member away from the fulcrum tensioner device imparts a first rotational force along the spine in a first direction.

20. The spinal construct of claim 19, wherein moving the second end of the tensioning member from the fulcrum tensioner device imparts a second rotational force along the spine in a second direction opposite from the first direction.

21. The spinal construct of claim 14, further comprising a tensioning instrument configured to apply tension to the tensioning member, the tensioning instrument including a tensioning screw and a clamping mechanism, the clamping mechanism including a clamp arm having a free position, in which the tensioning member is free to slide through the clamping mechanism, and a locked position, in which the tensioning member is fixed relative to the clamping mechanism, the tensioning screw configured to move the clamping mechanism away from one of the first and second fixation members to apply tension to the tensioning member when the clamping mechanism is in the locked position.

22. A spinal correction method comprising:
securing first and second fixation members to cranial and caudal vertebral bodies;
securing a fulcrum tensioner device to a vertebral body interposed between the cranial and caudal vertebral bodies;
inserting a portion of a tensioning member through a biasing member of the fulcrum tensioner device and looping around a camming pin operatively coupled with the biasing member to provide tension in the tensioning member, whereby a first end of the tensioning member is directed to a first direction and a second end of the tensioning member is directed to a second direction different from the first direction;
wrapping a first end portion of the tensioning member around a first vertebral body adjacent the cranial vertebral body;
wrapping a second end portion of the tensioning member around a second vertebral body adjacent the caudal vertebral body;
securing the first end portion of the tensioning member with the first fixation member; and
securing the second end portion of the tensioning member with the second fixation member.

23. The spinal correction method according to claim 22, wherein securing the fulcrum tensioner device includes positioning the fulcrum tensioner device adjacent an inflection point of a spinal curvature.

24. The spinal correction method according to claim 22, wherein securing the first end portion of the tensioning member includes extending at least a portion of the tensioning member through a cannulated shank of the first fixation member.

25. The spinal correction method according to claim 22, further comprising placing a release tab within a camming slot defined in a housing of the fulcrum tensioner device to compress the biasing member to inhibit application of tension to the tensioning member.

26. A spinal correction system comprising:
a tensioning member; and
a fulcrum tensioner device including:
a housing defining a chamber having a biasing member therein;
a divider operatively coupled with the biasing member, the divider defining a pair of slots configured to receive the tensioning member therethrough, the tensioning member configured to be received in the biasing member and looped through the divider, wherein the divider is transitionable between an extended position in which the biasing member applies tension to the tensioning member and a retracted position in which the biasing member is compressed; and
a securing portion with a bore and is attachable to the third vertebra using a screw inserted through the bore.

27. The spinal correction system according to claim 26, wherein the housing includes a body and a flange extending radially outward from the body, the body configured to be received in a vertebral body.

28. The spinal correction system according to claim 26, wherein the divider is biased towards the extended position.

* * * * *